US008251057B2

(12) United States Patent
Butler

(10) Patent No.: US 8,251,057 B2
(45) Date of Patent: Aug. 28, 2012

(54) HYPERBARIC CHAMBER CONTROL AND/OR MONITORING SYSTEM AND METHODS FOR USING THE SAME

(75) Inventor: Glenn Butler, Tarrytown, NY (US)

(73) Assignee: Life Support Technologies, Inc., Tarrytown, NY (US)

( * ) Notice: Subject to any disclaimer, the term of this patent is extended or adjusted under 35 U.S.C. 154(b) by 1555 days.

(21) Appl. No.: 10/880,676

(22) Filed: Jun. 30, 2004

(65) Prior Publication Data

US 2004/0261796 A1 Dec. 30, 2004

Related U.S. Application Data

(60) Provisional application No. 60/483,754, filed on Jun. 30, 2003.

(51) Int. Cl.
*A61G 10/00* (2006.01)
*A61M 15/00* (2006.01)
*B24D 13/00* (2006.01)
*G01L 7/00* (2006.01)
*H01G 7/00* (2006.01)

(52) U.S. Cl. ......... 128/202.12; 128/202.13; 128/202.14; 128/202.15; 128/202.16; 128/202.19; 128/205.26

(58) Field of Classification Search ............. 128/202.12, 128/202.13, 202.14, 202.15, 202.16, 202.19, 128/205.26; 454/70; 73/700, 714; 361/283.1, 361/283.2, 283.3
See application file for complete search history.

(56) References Cited

U.S. PATENT DOCUMENTS

| | | | |
|---|---|---|---|
| 3,394,415 | A | 7/1968 | Parker |
| 3,670,460 | A | 6/1972 | Oldfield et al. |
| 3,674,019 | A | 7/1972 | Grant |
| 3,678,520 | A | 7/1972 | Evans |
| 3,705,576 | A | 12/1972 | Roth |
| 3,745,998 | A | 7/1973 | Rose |
| 3,825,320 | A | 7/1974 | Redfern |
| 3,877,427 | A | 4/1975 | Alexeev et al. |
| 3,941,121 | A | 3/1976 | Olinger et al. |
| 4,127,319 | A | 11/1978 | Forney, Jr. et al. |
| 4,197,837 | A | 4/1980 | Tringali et al. |
| 4,267,611 | A | 5/1981 | Agulnick |

(Continued)

FOREIGN PATENT DOCUMENTS

| | | |
|---|---|---|
| CN | 2287698 | 8/1998 |

(Continued)

OTHER PUBLICATIONS

Dec. 15, 2009 Response to Office Action of U.S. Appl. No. 11/140,768 mailed Sep. 15, 2009.

(Continued)

*Primary Examiner* — Patricia Bianco
*Assistant Examiner* — Nihir Patel
(74) *Attorney, Agent, or Firm* — Dugan & Dugan, PC

(57) ABSTRACT

In a first aspect, a monoplace hyperbaric chamber providing Venturi induced gas circulation and ventilation is disclosed. The chamber includes a control and monitoring system that offers reduced oxygen consumption, duplex pressure gauges, referenced flow control, a patient activated stop function, an independent pressure time recorder, and/or a precise pressure control circuit that uses a 1:1 forced-balanced volume amplifier adapted to supply gas to and exhaust gas from the chamber through different penetrators and/or use flow-control check valves supplied with static reference or set pressures. A computer control and monitoring subsystem is also disclosed. Numerous other aspects are provided.

7 Claims, 8 Drawing Sheets

U.S. PATENT DOCUMENTS

| | | | | |
|---|---|---|---|---|
| 4,336,809 | A | 6/1982 | Clark | |
| 4,444,516 | A | 4/1984 | Dostoomian et al. | |
| 4,469,399 | A | 9/1984 | Cowen et al. | |
| 4,544,233 | A | 10/1985 | Iwamoto et al. | |
| 4,614,190 | A | 9/1986 | Stanco et al. | |
| 4,633,859 | A * | 1/1987 | Reneau | 128/205.26 |
| 4,653,130 | A | 3/1987 | Senoue et al. | |
| 4,682,846 | A | 7/1987 | Cowen | |
| 4,683,523 | A | 7/1987 | Olsson et al. | |
| 4,687,980 | A | 8/1987 | Phillips et al. | |
| 4,822,335 | A | 4/1989 | Kawai et al. | |
| 4,825,486 | A | 5/1989 | Kimura et al. | |
| 4,859,021 | A | 8/1989 | Wall | |
| 4,886,831 | A | 12/1989 | Morcos et al. | |
| 4,889,129 | A | 12/1989 | Dougherty et al. | |
| 4,891,640 | A | 1/1990 | Ip | |
| 4,930,504 | A | 6/1990 | Diamantopoulos et al. | |
| 4,932,934 | A | 6/1990 | Dougherty et al. | |
| 4,947,500 | A | 8/1990 | Seiler | |
| 4,957,481 | A | 9/1990 | Gatenby | |
| 4,977,361 | A | 12/1990 | Phillips et al. | |
| 5,012,609 | A | 5/1991 | Ignatius et al. | |
| 5,026,367 | A | 6/1991 | Leckrone et al. | |
| 5,041,108 | A | 8/1991 | Fox et al. | |
| 5,053,033 | A | 10/1991 | Clarke | |
| 5,054,867 | A | 10/1991 | Wagnieres et al. | |
| 5,060,644 | A | 10/1991 | Loori | |
| 5,098,426 | A | 3/1992 | Sklar et al. | |
| 5,103,518 | A | 4/1992 | Gilroy et al. | |
| 5,109,560 | A | 5/1992 | Uetake | |
| 5,109,561 | A | 5/1992 | Schild | |
| 5,146,917 | A | 9/1992 | Wagnieres et al. | |
| 5,151,096 | A | 9/1992 | Khoury | |
| 5,151,967 | A | 9/1992 | Ebinuma | |
| 5,163,898 | A | 11/1992 | Morcos et al. | |
| 5,243,723 | A | 9/1993 | Cotner et al. | |
| 5,253,321 | A | 10/1993 | Long et al. | |
| 5,257,970 | A | 11/1993 | Dougherty | |
| 5,267,364 | A | 12/1993 | Volk | |
| 5,278,432 | A | 1/1994 | Ignatius et al. | |
| 5,298,018 | A | 3/1994 | Narciso | |
| 5,401,270 | A | 3/1995 | Muller et al. | |
| 5,413,587 | A | 5/1995 | Hochstein | |
| 5,445,608 | A | 8/1995 | Chen et al. | |
| 5,454,794 | A | 10/1995 | Narciso et al. | |
| 5,466,234 | A | 11/1995 | Loeb et al. | |
| 5,503,143 | A | 4/1996 | Marion et al. | |
| 5,562,656 | A | 10/1996 | Sumiya | |
| 5,573,531 | A | 11/1996 | Gregory | |
| 5,582,574 | A | 12/1996 | Cramer | |
| 5,584,085 | A | 12/1996 | Banko | |
| 5,592,706 | A | 1/1997 | Pearce | |
| 5,623,736 | A | 4/1997 | Soltani et al. | |
| 5,645,550 | A | 7/1997 | Hohla | |
| 5,649,972 | A | 7/1997 | Hochstein | |
| 5,651,783 | A | 7/1997 | Reynard | |
| 5,660,461 | A | 8/1997 | Ignatius et al. | |
| 5,685,036 | A | 11/1997 | Kopfstein et al. | |
| 5,685,293 | A * | 11/1997 | Watt | 128/202.27 |
| 5,698,866 | A | 12/1997 | Doiron et al. | |
| 5,725,522 | A | 3/1998 | Sinofsky | |
| 5,728,090 | A | 3/1998 | Martin et al. | |
| 5,762,867 | A | 6/1998 | D'Silva | |
| 5,794,289 | A | 8/1998 | Wortman et al. | |
| 5,860,967 | A | 1/1999 | Zavislan et al. | |
| 5,865,832 | A | 2/1999 | Knopp et al. | |
| 5,873,137 | A | 2/1999 | Yavets-Chen | |
| 5,901,393 | A | 5/1999 | Pepe et al. | |
| 5,902,328 | A | 5/1999 | LaFontaine et al. | |
| 5,918,336 | A | 7/1999 | Lee et al. | |
| 5,938,657 | A | 8/1999 | Assa et al. | |
| 5,944,748 | A | 8/1999 | Mager et al. | |
| 5,963,997 | A | 10/1999 | Hagopian | |
| 5,983,428 | A | 11/1999 | Hannagan | |
| 5,989,245 | A | 11/1999 | Prescott | |
| 6,011,563 | A | 1/2000 | Fournier et al. | |
| 6,019,482 | A | 2/2000 | Everett | |
| 6,048,359 | A | 4/2000 | Biel | |
| 6,062,215 | A | 5/2000 | Leininger et al. | |
| 6,073,289 | A | 6/2000 | Bolden et al. | |
| 6,099,522 | A | 8/2000 | Knopp et al. | |
| 6,152,919 | A | 11/2000 | Hakky | |
| 6,197,099 | B1 | 3/2001 | Pearce | |
| 6,203,540 | B1 | 3/2001 | Weber | |
| 6,203,542 | B1 | 3/2001 | Ellsberry et al. | |
| 6,206,654 | B1 | 3/2001 | Cassidy | |
| 6,210,425 | B1 | 4/2001 | Chen | |
| 6,221,095 | B1 | 4/2001 | Van Zuylen et al. | |
| 6,241,697 | B1 | 6/2001 | Augustine | |
| 6,290,713 | B1 | 9/2001 | Russell | |
| 6,308,353 | B1 | 10/2001 | Van Steenburg | |
| 6,326,550 | B1 | 12/2001 | Dyer et al. | |
| 6,334,069 | B1 | 12/2001 | George et al. | |
| 6,344,050 | B1 | 2/2002 | Chen | |
| 6,353,763 | B1 | 3/2002 | George et al. | |
| 6,353,948 | B1 | 3/2002 | Bolden et al. | |
| 6,374,031 | B1 | 4/2002 | Nelms, Jr. | |
| 6,402,681 | B1 | 6/2002 | McDonough et al. | |
| 6,443,978 | B1 | 9/2002 | Zharov | |
| 6,484,716 | B1 | 11/2002 | Leininger et al. | |
| 6,497,231 | B1 | 12/2002 | White | |
| 6,511,414 | B1 | 1/2003 | Hamsund | |
| 6,605,082 | B2 | 8/2003 | Hareyama et al. | |
| 6,618,620 | B1 | 9/2003 | Freundlich et al. | |
| 6,641,578 | B2 | 11/2003 | Mukai | |
| 6,669,684 | B2 | 12/2003 | Nakamura | |
| 6,676,654 | B1 | 1/2004 | Balle-Petersen et al. | |
| 6,697,664 | B2 | 2/2004 | Kienzle, III et al. | |
| 6,789,284 | B2 | 9/2004 | Kemp | |
| 6,979,328 | B2 | 12/2005 | Baerveldt et al. | |
| 7,001,413 | B2 | 2/2006 | Butler | |
| 7,201,766 | B2 | 4/2007 | Butler | |
| 7,270,593 | B2 | 9/2007 | Klein et al. | |
| 7,367,342 | B2 | 5/2008 | Butler | |
| 7,386,339 | B2 | 6/2008 | Strommer et al. | |
| 2002/0026180 | A1 | 2/2002 | Nakamura | |
| 2002/0120312 | A1 | 8/2002 | Ignatius et al. | |
| 2002/0173833 | A1 | 11/2002 | Korman et al. | |
| 2003/0004499 | A1 | 1/2003 | McDaniel | |
| 2003/0159700 | A1 | 8/2003 | Laufer et al. | |
| 2004/0068305 | A1 | 4/2004 | Bansal et al. | |
| 2004/0098069 | A1 | 5/2004 | Clement et al. | |
| 2004/0158300 | A1 | 8/2004 | Gardiner | |
| 2004/0215176 | A1 | 10/2004 | Bahk | |
| 2005/0262639 | A1 | 12/2005 | Butler | |
| 2006/0111761 | A1 | 5/2006 | Butler | |
| 2007/0073365 | A1 | 3/2007 | Butler | |
| 2008/0281383 | A1 | 11/2008 | Butler | |

FOREIGN PATENT DOCUMENTS

| | | | |
|---|---|---|---|
| DE | 3837248 | | 5/1990 |
| EP | 0237046 | B1 | 9/1987 |
| GB | 2164137 | | 3/1986 |
| IT | 1266185 | B1 | 12/1996 |
| WO | WO 86/02244 | | 4/1986 |
| WO | WO 9920988 | | 4/1999 |
| WO | WO 01/89348 | A3 | 11/2001 |
| WO | WO 02/39558 | A2 | 5/2002 |

OTHER PUBLICATIONS

Dec. 29, 2009 Response to Final Office Action of U.S. Appl. No. 12/115,371 mailed Oct. 29, 2009.

Notice of Abandonment of U.S. Appl. No. 11/329,513 mailed Dec. 29, 2009.

Advisory Action of U.S. Appl. No. 12/115,371 mailed Feb. 3, 2010.

Notice of Allowance of U.S. Appl. No. 11/140,768 mailed Mar. 5, 2010.

Notice of Allowance of U.S. Appl. No. 11/560,685 mailed Mar. 22, 2010.

Office Action of U.S. Appl. No. 10/613,608 mailed Jun. 7, 2004.

Sep. 7, 2004 Response to Office Action of U.S. Appl. No. 10/613,608 mailed Jun. 7, 2004.

Office Action of U.S. Appl. No. 10/613,608 mailed Nov. 3, 2004.

Mar. 3, 2005 Response to Office Action of U.S. Appl. No. 10/613,608 mailed Nov. 3, 2004.

Final Office Action of U.S. Appl. No. 10/613,608 mailed Mar. 18, 2005.
Jul. 18, 2005 Response to Final Office Action of U.S. Appl. No. 10/613,608 mailed Mar. 18, 2005.
Advisory Action of U.S. Appl. No. 10/613,608 mailed Aug. 4, 2005.
Aug. 18, 2005 Response to Final Office Action of U.S. Appl. No. 10/613,608 mailed Mar. 18, 2005.
Notice of Allowance of U.S. Appl. No. 10/613,608 mailed Sep. 6, 2005.
Office Action of U.S. Appl. No. 11/329,513 mailed Jul. 14, 2008.
Nov. 17, 2008 Response to Office Action of U.S. Appl. No. 11/329,513 mailed Jul. 14, 2008.
Final Office Action of U.S. Appl. No. 11/329,513 mailed Jun. 9, 2009.
Office Action of U.S. Appl. No. 10/726,028 mailed Dec. 29, 2006.
Mar. 28, 2007 Response to Office Action of U.S. Appl. No. 10/726,028 mailed Dec. 29, 2006.
Final Office Action of U.S. Appl. No. 10/726,028 mailed Jul. 13, 2007.
Oct. 15, 2007 Response to Final Office Action of U.S. Appl. No. 10/726,028 mailed Jul. 13, 2007.
Notice of Allowance of U.S. Appl. No. 10/726,028 mailed Dec. 26, 2007.
Office Action of U.S. Appl. No. 12/115,371 mailed Apr. 1, 2009.
Jul. 1, 2009 Response to Office Action of U.S. Appl. No. 12/115,371 mailed Apr. 1, 2009.
Final Office Action of U.S. Appl. No. 12/115,371 mailed Oct. 29, 2009.
Office Action of U.S. Appl. No. 10/726,040 mailed Aug. 9, 2005.
Nov. 10, 2005 Response to Office Action of U.S. Appl. No. 10/726,040 mailed Aug. 9, 2005.
Office Action of U.S. Appl. No. 10/726,040 mailed Jan. 4, 2006.
Apr. 4, 2006 Response to Office Action of U.S. Appl. No. 10/726,040 mailed Jan. 4, 2006.
Final Office Action of U.S. Appl. No. 10/726,040 mailed May 16, 2006.
Sep. 18, 2006 Response to Final Office Action of U.S. Appl. No. 10/726,040 mailed May 16, 2006.
Advisory Action of U.S. Appl. No. 10/726,040 mailed Sep. 27, 2006.
Nov. 16, 2006 Response to Final Office Action of U.S. Appl. No. 10/726,040 mailed May 16, 2006.
Notice of Allowance of U.S. Appl. No. 10/726,040 mailed Nov. 29, 2006.
Office Action of U.S. Appl. No. 11/560,685 mailed Feb. 13, 2009.
Apr. 16, 2009 Response to Office Action of U.S. Appl. No. 11/560,685 mailed Feb. 13, 2009.
Office Action of U.S. Appl. No. 11/560,685 mailed Aug. 19, 2009.
Nov. 6, 2009 Response to Office Action of U.S. Appl. No. 11/560,685 mailed Aug. 19, 2009.
Office Action of U.S. Appl. No. 11/140,768 mailed Mar. 19, 2007.
Jun. 19, 2007 Response to Office Action of U.S. Appl. No. 11/140,768 mailed Mar. 19, 2007.
Final Office Action of U.S. Appl. No. 11/140,768 mailed Sep. 11, 2007.
Jan. 16, 2008 Response to Final Office Action of U.S. Appl. No. 11/140,768 mailed Sep. 11, 2007.
Final Office Action of U.S. Appl. No. 11/140,768 mailed Feb. 11, 2008.
Jun. 11, 2008 Response to Final Office Action of U.S. Appl. No. 11/140,768 mailed Feb. 11, 2008.
Advisory Action of U.S. Appl. No. 11/140,768 mailed Jul. 1, 2008.
Jul. 11, 2008 Response to Final Office Action of U.S. Appl. No. 11/140,768 mailed Feb. 11, 2008.
Office Action of U.S. Appl. No. 11/140,768 mailed Aug. 19, 2008.
Feb. 18, 2009 Response to Office Action of U.S. Appl. No. 11/140,768 mailed Aug. 19, 2008.
Final Office Action of U.S. Appl. No. 11/140,768 ailed May 29, 2009.
Aug. 31, 2009 Response to Final Office Action of U.S. Appl. No. 11/140,768 mailed May 29, 2009.
Office Action of U.S. Appl. No. 11/140,768 mailed Sep. 15, 2009.
Whelan et al., "NASA Light Emitting Diode Medical Applications From Deep Space to Deep Sea," Space Technology and Applications International Forum—2001, American Institute of Physics, pp. 35-45 (2001).
Notice of Abandonment of U.S. Appl. No. 12/115,371 mailed Jun. 8, 2010.
Supplemental Notice of Allowance of U.S. Appl. No. 11/140,768 mailed Jun. 24, 2010.
Terminal Disclaimer of Patent No. 7,001,413 filed in U.S. Appl. No. 11/329,513, filed Nov. 17, 2008.
Notice of Non-Compliant Amendment of U.S. Appl. No. 11/329,513 mailed Feb. 4, 2009.
Terminal Disclaimer of Patent No. 7,001,413 filed in US Appl. No. 11/329,513 filed Mar. 4, 2009.
Applicant Summary of Interview with Examiner filed in U.S. Appl. No. 12/115,371, filed Dec. 29, 2009.
Terminal Disclaimer of Patent No. 7,201,766 filed in U.S. Appl. No. 11/560,685, filed Apr. 16, 2009.
Applicant Summary of Interview with Examiner filed in U.S. Appl. No. 11/140,768, filed Jan. 16, 2008.
Butler et al., U.S. Appl. No. 13/078,776, filed Apr. 1, 2011.

* cited by examiner

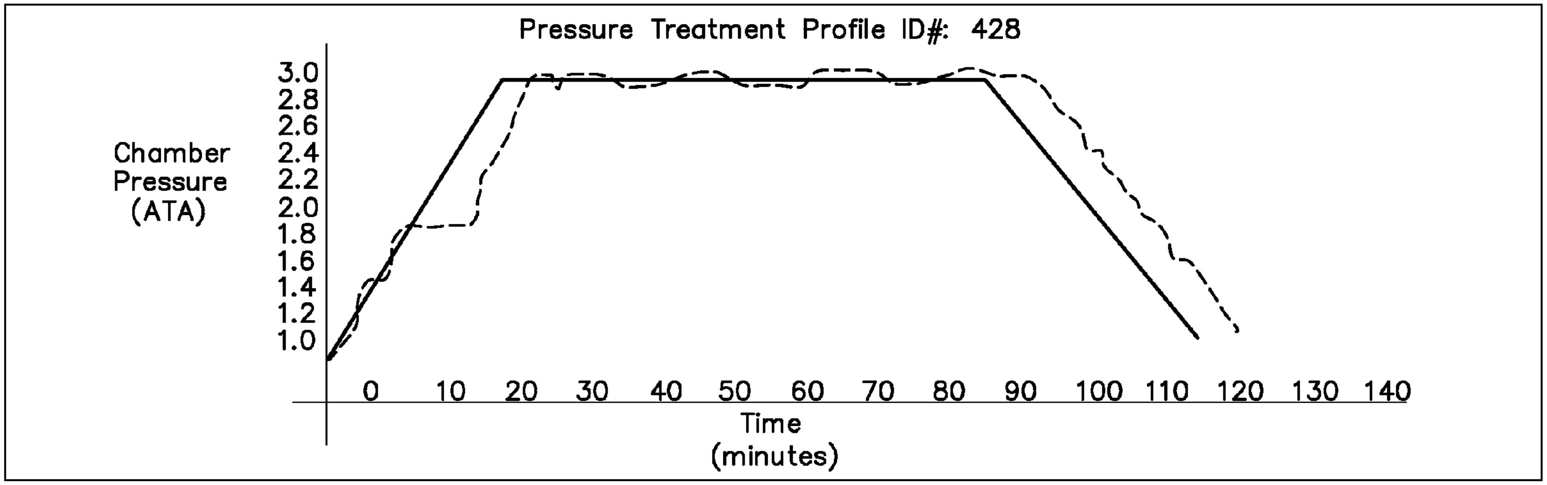

| | |
|---|---|
| Patient Name: | Jane Doe |
| Date of Birth: | 7/14/66 |
| Social Security Number: | 046–21–3478 |
| Medical Record Number: | 89765–23 |
| Date of service: | 2/18/06 |
| Diagnosis: | Gas Gangrene (ICD–9 40.0) |
| HBO Treatment ID#: | 0629–5 |
| HBO TX Profile Type: | 3.0 ATA for 70 minutes |

| Patient Vital Signs | Pre Tx | Post Tx |
|---|---|---|
| Heart Rate | 110 (NH) | 130 (H) |
| Blood Pressure | 120/90 (NH) | 120/70 (N) |
| Temperature | 103.0 (H) | 103.6 (H) |
| Glucose | 260 (NH) | 180 (N) |
| Last Meal | 08:30 | |
| Standard/Modified Profile | (M) | |
| Light Therapy Profile 1–10 | (6) | |

Chamber Operator: Smith
Physician of Record: Jones

FIG. 6

HYPERBARIC CHAMBER CONTROL AND/OR MONITORING SYSTEM AND METHODS FOR USING THE SAME

This application claims priority from U.S. Provisional Patent Application No. 60/483,754, filed Jun. 30, 2003 and entitled “HYPERBARIC CHAMBER CONTROL AND/OR MONITORING SYSTEM AND METHODS FOR USING THE SAME” which is incorporated herein by reference in its entirety for all purposes.

FIELD OF THE INVENTION

The present invention relates generally to hyperbaric chambers, and more particularly to a hyperbaric chamber control and/or monitoring system and methods for using the same.

BACKGROUND OF THE INVENTION

Monoplace hyperbaric chambers are designed to provide oxygen therapy under a specific pressure profile for one patient at a time. Such chambers typically have basic pressure control and monitoring systems. A commercially available example of a conventional chamber is the Model 3200 Monoplace Hyperbaric Chamber manufactured by Sechrist Industries, Inc. of Anaheim, Calif. These chambers typically include a series of manual gas valves that allow an operator to control input pressure, ventilation, and exhaust. Conventional chambers require the use of a large volume of oxygen in order to maintain the desired pressure while attempting to provide adequate ventilation to control carbon dioxide and water vapor and provide patient cooling. For example, a typical prior art monoplace hyperbaric chamber uses 200 to 500 liters per minute of oxygen.

Turning to FIG. 1, a pneumatic schematic illustrating a convention system 100 of flow control gas valves for a typical prior art hyperbaric chamber 102 is depicted. An oxygen supply 104 feeds the chamber 102 with oxygen to create compression in the chamber 102. The desired amount of oxygen is applied at a rate controlled via a pressure flow control valve 106. The pressure flow control valve 106 is itself controlled by a pneumatic control signal that may be adjusted to an appropriate pressure by referencing a pressure gauge 108. A regulator 110 is used to actually send the pneumatic control signal to the pneumatic control of the pressure flow control valve 106 to allow more or less oxygen into the chamber 102. The operator must carefully monitor the chamber pressure by watching the chamber pressure gauge 120 relative to the pneumatic control signal on the first pressure gauge 108.

In addition to the pressure flow control valve 106, a ventilation flow control valve 112 is used to provide additional oxygen to the chamber 102 for ventilation. The ventilation flow control valve 112 is controlled based upon the current amount of pressure in the chamber 102 via a feedback pneumatic control signal to the ventilation flow control valve 112.

An exhaust flow control valve 114 (e.g., a back pressure flow control valve) vents air from the chamber 102 at a rate that is slow enough to maintain the desired pressure within the chamber 102 but fast enough to both meet a required ventilation rate and help maintain a desired temperature range within the chamber 102. Thus, the pneumatic control of the exhaust flow control valve 114 also receives a feedback pneumatic control signal based upon the current amount of pressure in the chamber 102. Finally, the exhaust circuit also includes a manual bypass exhaust flow control valve 116 and a flow meter 118 to allow manual release of compressed air from the chamber 102 at a manually controlled rate.

A significant problem with prior art hyperbaric chamber control systems is that they require equally zeroed and calibrated pressure gauges at atmospheric pressure to not read the same pressures for a given treatment depth. For example, the prior art requires a substantial (e.g., ½ to 1 PSIG) differential between a lower set pressure and a desired chamber treatment pressure in order for the prior art system to provide a 200 lpm+ ventilation rate. This necessary miscalibration has often resulted in operator confusion due to the difference between the gauges which may result in operator error that may compromise patient care.

As depicted in FIG. 2, in prior art hyperbaric chambers 102, incoming oxygen will find the least resistive route 200 to the exhaust port. This phenomenon is referred to as a channeling effect. Unless a very high volume (e.g., 200+ lpm) of oxygen is forced into the prior art chamber 102, the majority of the oxygen in the chamber 102 being exhausted will bypass the patient 202 and flow below or between the stretcher 204 and the chamber hull. Below 200 lpm prior art chambers fail to ventilate causing fogging due to water vapor from the patient's breathing and causing a build-up of carbon dioxide in the chamber 102. Thus, prior art chambers 102 must use a high volume of oxygen to insure adequate circulation of oxygen within the chamber 102. This further contributes to the inefficiency of prior art hyperbaric chambers 102. In many prior art chambers 102, adequate circulation is not only important in order to provide the patient 202 with sufficient oxygen for breathing and to remove exhaled carbon dioxide and water vapor, but also to maintain a comfortable temperature throughout the chamber 102.

In many areas of the world, medical grade compressed oxygen suitable for use in a hyperbaric chamber 102 is expensive and not readily available. Thus, it is a substantial drawback of prior art chambers 102 that they must use high volumes of oxygen. In addition, using such high volumes of oxygen results in significant noise levels within the chamber 102 which may be unpleasant for patients that may be subjected to the loud noise for prolonged periods during treatment. Thus, what is needed is a monoplace hyperbaric chamber and control system that does not suffer from the above described drawbacks.

SUMMARY OF THE INVENTION

In accordance with some embodiments of the invention, there is provided a control system for a hyperbaric chamber including a patient control mechanism adapted to allow a patient to affect compression and/or decompression of the hyperbaric chamber while the patient is located within the chamber.

In accordance with some embodiments of the invention, there is provided a pneumatic compression circuit including a volume booster operable to pressurize, depressurize, and hold a pressure within a hyperbaric chamber, and a ventilation circuit coupled to the hyperbaric chamber.

In accordance with some embodiments of the invention, there is provided a method including discharging cooled gas at the outlet end of a Venturi duct within a hyperbaric chamber so as to entrain gas in the hyperbaric chamber into the inlet end of the Venturi duct.

In accordance with some embodiments of the invention, there is provided a method including discharging gas at the outlet end of a Venturi duct within a hyperbaric chamber, directing the gas to flow past a patient's head disposed within the hyperbaric chamber, and entraining the gas to re-circulate within the hyperbaric chamber via the Venturi duct.

In accordance with some embodiments of the invention, there is provided a method including ventilating a hyperbaric chamber using cooled gas and circulating the cooled gas within the hyperbaric chamber using a Venturi duct.

In accordance with some embodiments of the invention, there is provided a Venturi duct disposed within a hyperbaric chamber, a gas supply line coupled to the Venturi duct, and a heat exchanger disposed proximate to the gas supply line.

In accordance with some embodiments of the invention, there is provided a flow controller coupled between a pressurized gas supply and a hyperbaric chamber. The flow controller includes a signal port coupled to an outlet port of a set pressure selection valve. A duplex analog pressure gauge is coupled to the hyperbaric chamber and an outlet port of the set pressure selection valve. In some embodiments, the set pressure selection valve includes a computer controlled regulator valve.

In accordance with some embodiments of the invention, there is provided a hyperbaric chamber having an inlet port and an exhaust port wherein the ports each include a one-way valve, and a volume booster is coupled to both the inlet port and the exhaust port of the hyperbaric chamber. An inlet port of the volume booster may be coupled to a pressurized gas supply. In some embodiments, a ventilation circuit may also be coupled to the hyperbaric chamber. In some embodiments, the volume booster includes a 1:1 forced-balanced volume amplifier. In some embodiments, a signal port of the volume booster is coupled to an outlet port of a set pressure selection valve. In some embodiments, the set pressure selection valve includes a computer controlled regulator valve.

In accordance with some embodiments of the invention, there is provided a flow controller that may be coupled between a pressurized gas supply and a valve wherein the flow controller includes a reference port coupled to an outlet port of the valve and to a one-way inlet port of a hyperbaric chamber. In some embodiments, the flow controller is coupled to a primary ventilation gas, a focused ventilation gas, and/or a mask gas. In some embodiments, the valve includes a control coupled to, and operable by, an electric-to-pneumatic transducer coupled to a computer controller.

In accordance with some embodiments of the invention, there is provided a pneumatic control system for a monoplace hyperbaric chamber, a computer control system coupled to the pneumatic control system via a plurality of transducers, and a program operable to execute a hyperbaric treatment profile selected from among a database of treatment profiles based upon a plurality of characteristics of a patient.

Further features and advantages of the present invention will become more fully apparent from the following detailed description, the appended claims and the accompanying drawings.

BRIEF DESCRIPTION OF THE DRAWINGS

FIG. 6 is an illustration of an example user interface of a computer monitoring and control subsystem for a pneumatic system for a monoplace hyperbaric chamber according to some embodiments of the present invention.

DETAILED DESCRIPTION

The present invention provides specific and significant improvements in pressure control, lower oxygen consumption, temperature and humidity environmental control, and safety as compared to control systems of prior art monoplace hyperbaric chambers presently available in the worldwide marketplace.

Figure 3:
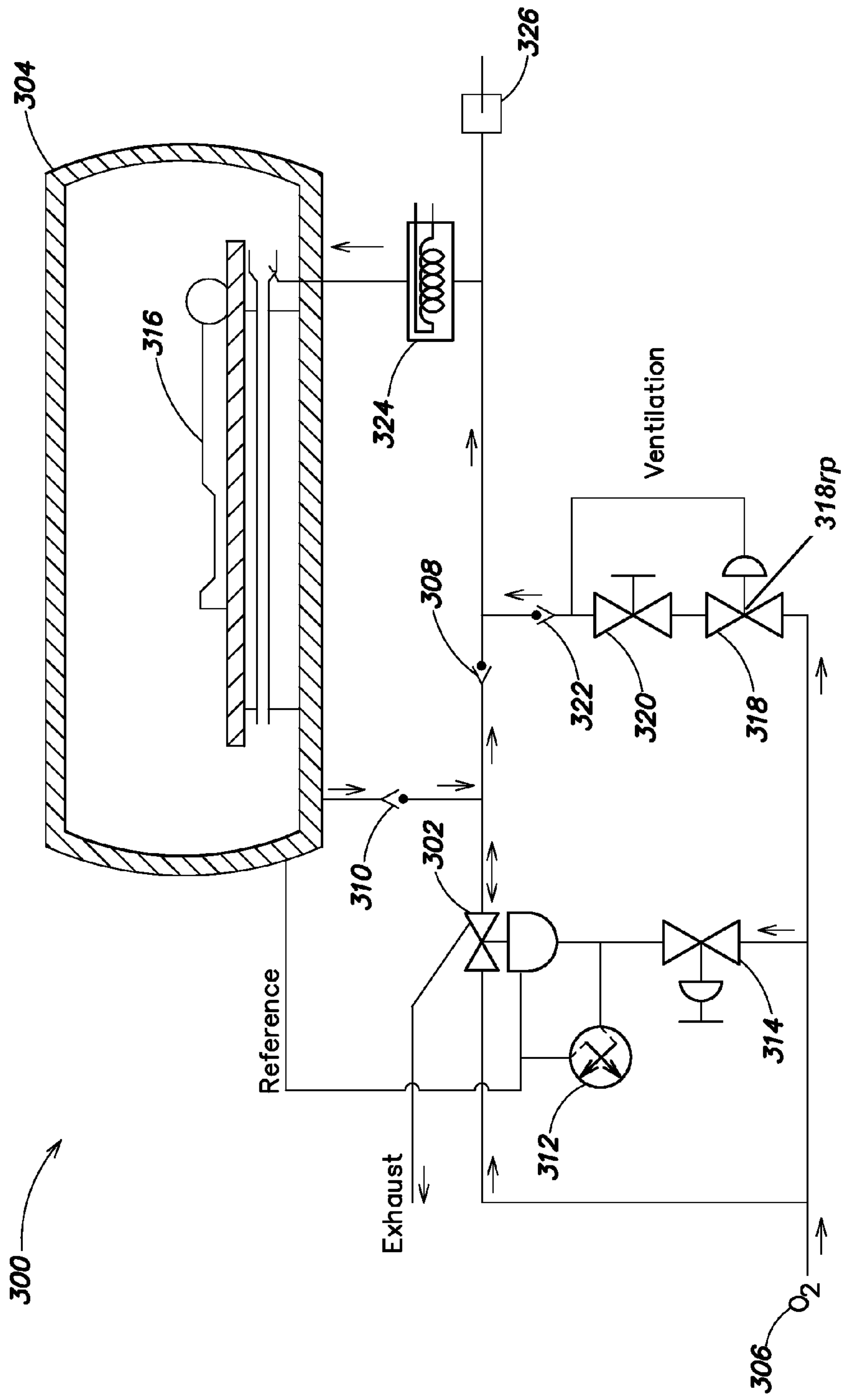
FIG. 3 is a schematic diagram of a portion of an example pneumatic control system for a monoplace hyperbaric chamber according to some embodiments of the present invention.

As illustrated in FIG. 3, in some embodiments of the present invention a hyperbaric chamber control system 300 uses, for example, a pneumatic volume booster 302 to both provide oxygen to pressurize the chamber 304 and to provide controlled exhaust of the chamber 304. The inlet port of the booster 302 is coupled to an oxygen supply 306 and the outlet port of the booster 302 is coupled to a check valve 308 leading to the chamber 304. The check valve 308 prevents oxygen from flowing back from the chamber 304.

The outlet port of the booster 302 is also coupled to a check valve 310 leading from an exhaust outlet of the chamber 304. Check valve 310 (e.g., a gravity swing check valve such as model number T-473 (class 200) manufactured by Nibco Inc. of Elkhart, Ind.) prevents oxygen from flowing back into the chamber via the chamber's exhaust port.

The signal port of the booster 302 is coupled to a duplex analog pressure gauge 312 and the outlet port of a flow control valve 314 that can be used to send a one to one ratio pneumatic signal to control the pneumatic volume booster 302. The flow control valve 314 also is referred to herein as a set pressure selection valve. The duplex analog pressure gauge 312 is used to insure that the proper pressure control signal is sent to the volume booster 302 while simultaneously and intuitively allowing the operator to monitor the chamber pressure. The inlet of the flow control valve 314 is coupled to the oxygen supply 306. The remote feedback port of the booster 302 is coupled to the chamber 304 to provide a reference pressure level to the booster 302.

In operation, the booster 302 discharges gas at a higher pressure then the set point pressure coming from flow controller 314 in order to fill the chamber 304 with gas. Once the chamber pressure exceeds the set point pressure, the booster 302 shuts off the oxygen being supplied to the chamber 304. This dynamic would result in the chamber being pressurized to an extent greater than the set point pressure. However, the line leading from the chamber 304 to the remote feedback port of the booster 302 allows the booster 302 to sense the chamber pressure and compare it to the set point pressure independent of the booster's discharge pressure. This prevents the booster 302 from undesirably over shooting the set point pressure.

When increased pressure is needed in the chamber 304, the volume booster 302 is signaled to allow additional oxygen in through check valve 308. When decreased pressure is needed in the chamber 304, the volume booster 302 is signaled to allow air out through check valve 310 and via its exhaust port. When constant pressure is needed in the chamber 304, the volume booster 302 is signaled to exhaust only an amount of air equivalent to the amount of oxygen being added for ventilation. The control system 300 of the present invention thus, conserves the pressurized oxygen within the chamber 304 by only exhausting the minimum amount of oxygen required to avoid increasing the pressure from oxygen added by the ventilation circuit (discussed below). As will be explained below, additional oxygen for cooling and circulation is not required by the hyperbaric chamber 304 of the present invention.

A commercially available example of a pneumatic volume booster 302 that may be suitable for use with some embodiments of the present invention includes the Model 4500A (Part No. EA19549-1EI) Pneumatic Volume Booster (with tapped exhaust, remote feedback port, and bypass valve options) manufactured by the Fairchild Industrial Products Company of Winston-Salem, N.C. In some embodiments, other components may be used in place of the pneumatic volume booster 302 to provide both compression and exhaust of the chamber 304.

In some embodiments of the present invention, a ventilation circuit provides a steady flow of additional oxygen to the chamber 304 to insure that a patient 316 undergoing treatment in the chamber 304 continuously receives sufficient fresh oxygen to reduce/minimize any accumulation of carbon dioxide and water vapor. A ventilation circuit suitable for use in some embodiments of the present invention includes a ventilation flow controller 318 coupled to the oxygen supply 306. The outlet port of the ventilation flow controller 318 may be coupled to a metering valve 320 (e.g., a needle valve) which is coupled to a check valve 322 leading to the hyperbaric chamber 304. The reference port 318*rp* of the ventilation flow controller 318 is coupled to the outlet of the metering valve 320 to provide a feedback pressure level to automatically compensate for changes in the chamber pressure. Commercially available examples of a ventilation flow controller 318 and compatible metering valve 320 that may be suitable for use with some embodiments of the present invention include the Series 63 Constant Differential Flow Controllers manufactured by Siemens Energy & Automation, Inc. of Alpharetta, Ga.

In some embodiments of the present invention, a heat exchanger 324 is used to cool the oxygen entering the chamber 304 down to, for example, thirty-five degrees Fahrenheit (or another desired temperature). The heat exchanger 324 may be disposed within the chamber or in the line leading from the check valves 308, 322. In some embodiments, the heat exchanger may be located in other positions. The heat exchanger 324 further reduces consumption of oxygen in that in the system 300 of the present invention, cooled oxygen keeps the patient comfortable instead of using a high volume of oxygen to achieve the same result. A commercially available example of a heat exchanger 324 that may be suitable for use with some embodiments of the present invention includes the Type P-30 Plate Heat Exchanger manufactured by Delaval International AB of Tumba, Sweden.

In some embodiments of the present invention, a door safety lock 326 prevents the door of the hyperbaric chamber 304 from opening while the chamber 304 is under pressure. A commercially available example of a door safety lock 326 that may be suitable for use with some embodiments of the present invention includes oxygen-compatible spring return stainless steel pneumatic cylinder manufactured by Bimba Manufacturing Company of Monee, Ill.

Figure 1:
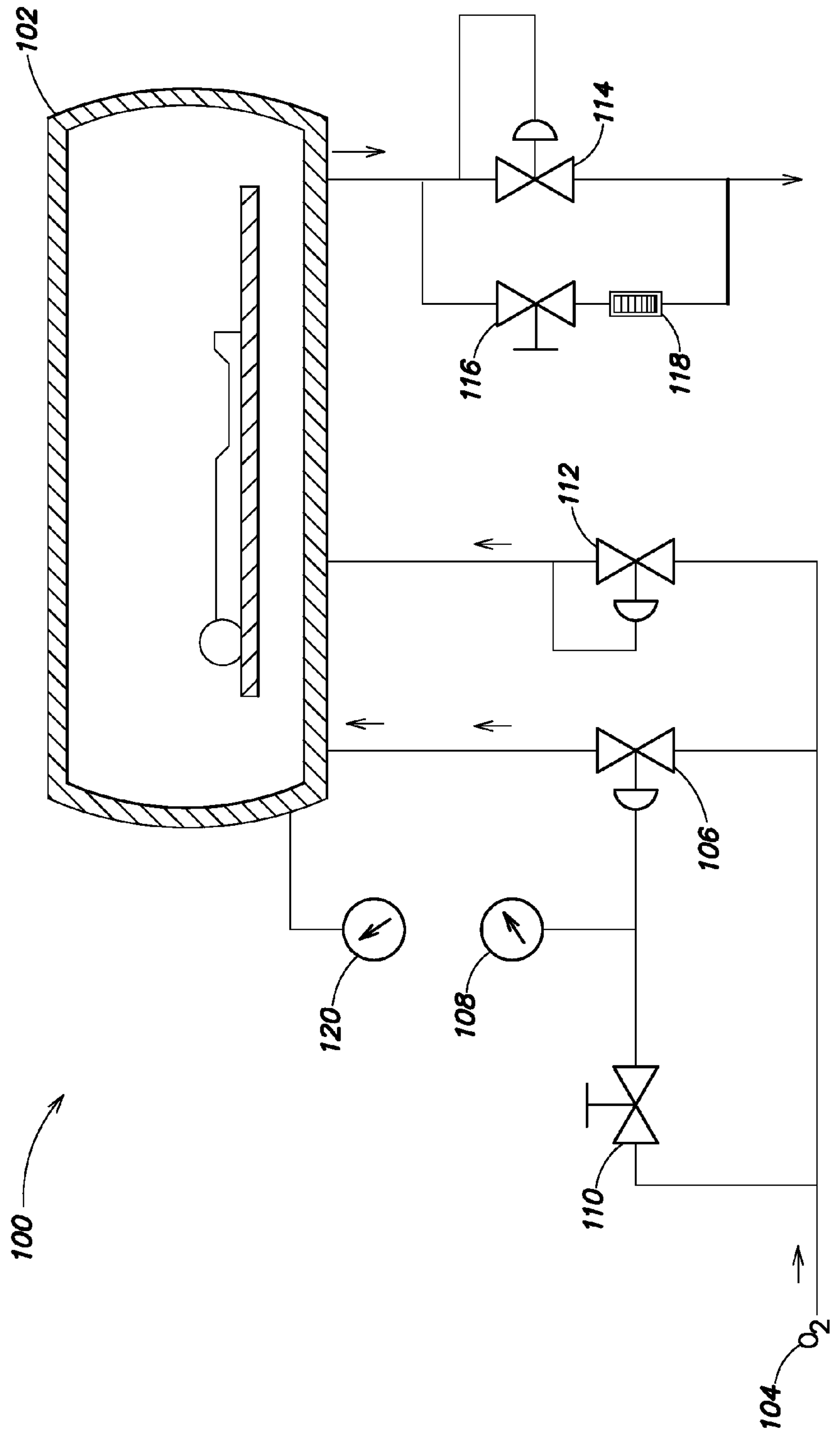
FIG. 1 (Prior Art)
FIG. 1 is a schematic diagram of a conventional pneumatic control system for a prior art monoplace hyperbaric chamber.
Figure 2:
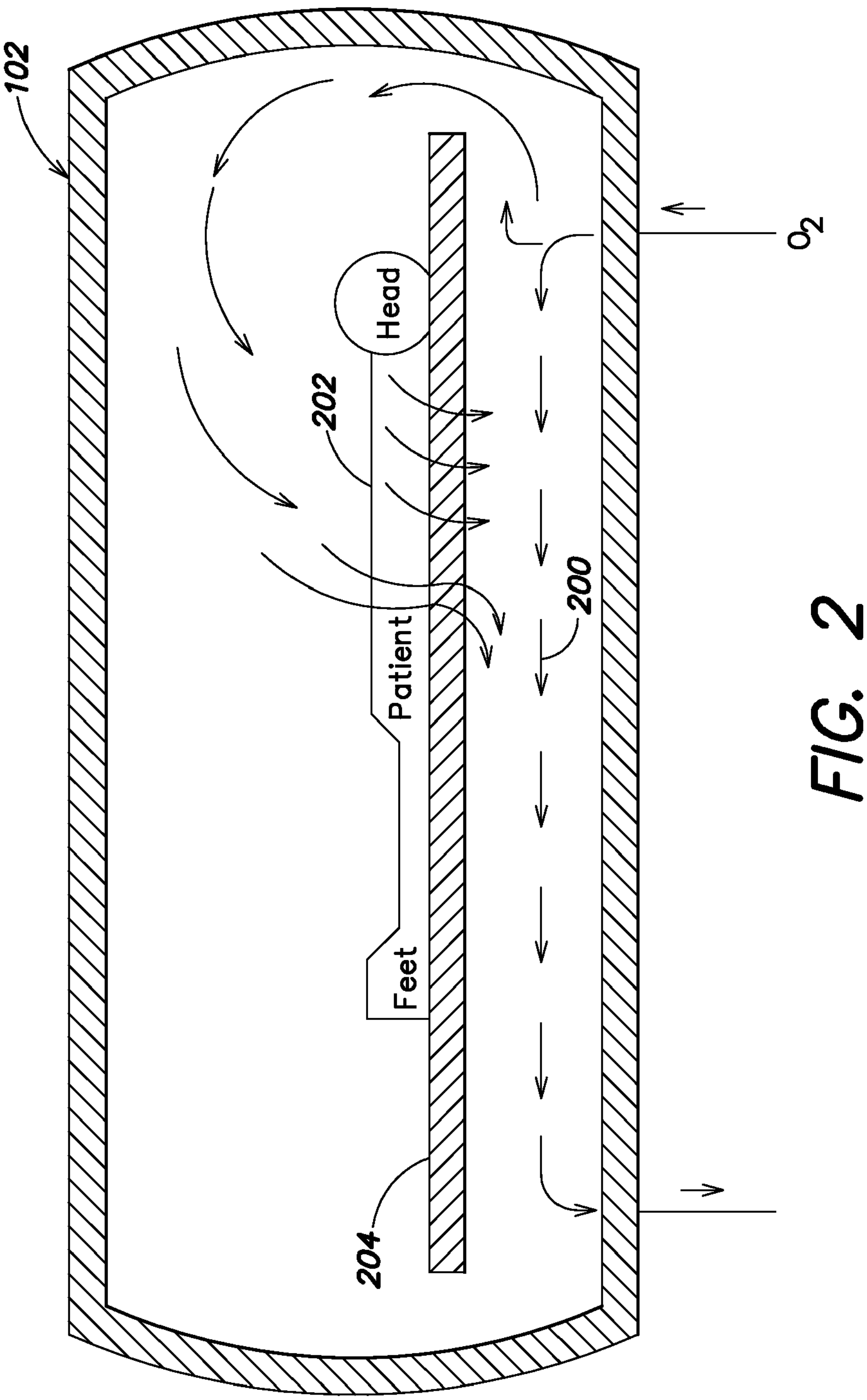
FIG. 2 (Prior Art)
FIG. 2 is a cross-sectional side view diagram of a prior art monoplace hyperbaric chamber.
Figure 4:
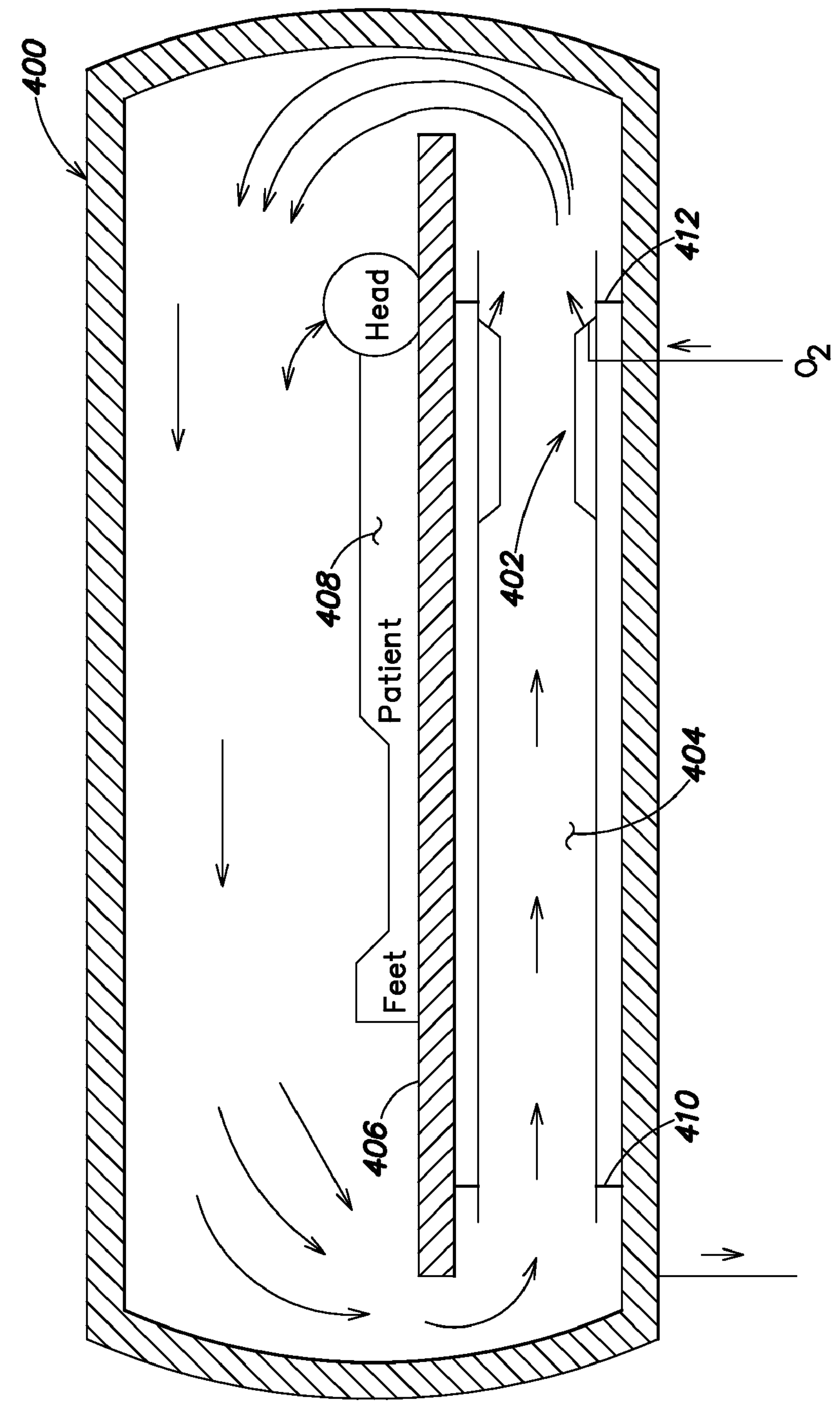
FIG. 4 is a cross-sectional side view diagram of an example monoplace hyperbaric chamber according to some embodiments of the present invention.

Turning to FIG. 4, a diagram illustrating a cross-sectional view of an example hyperbaric chamber 400 (including Venturi induced circulation of oxygen along the long axis of the example chamber 400) of some embodiments of the present invention is depicted. In contrast to the prior art hyperbaric chamber depicted in FIG. 2, oxygen circulation throughout the chamber 400 of the present invention is much more uniform and substantial for a given volume of freshly supplied oxygen and thus, ventilation is more efficient.

For example, prior art chambers require significant ventilation rates of over 200 liters per minute (LP/M) to exchange the atmospheric air within the chamber after closing the door and beginning compression with the therapeutic oxygen gas. 95% oxygen is considered a therapeutic concentration at 2 atmospheres absolute (ATA). Typically prior art chambers take over six minutes from closing the door to reaching 2 ATA and 95% oxygen concentration at 200 LP/M flow rates. In addition, prior art chambers at 2 ATA require up to seven minutes to change the chamber mixture being breathed by the patient from air at 1 ATA to 98% Oxygen at 2 ATA- even at 200 LP/M due to the inefficient gas flow design. (This type of change may be used after providing the patient with an "air break" to prevent a seizure.)

In the event of patient oxygen seizure at 2 ATA some operational protocols recommend switching to air (21% Oxygen, 79% Nitrogen) to interrupt the patient oxygen induced grand mal seizure. Prior art chambers are unable to shift from one gas to another without significant delay. For example, at the normal minimal flow rate of 200 LP/M, the Sechrist 3200 chamber takes over eight minutes to change from pure oxygen to 21% oxygen air at a pressure of 2 ATA. At higher (& noisier) ventilation rates of 400 LP/M this time only improves to six minutes.

Referring to FIG. 4, a chamber inlet port provides oxygen to the expanding outlet of a Venturi tube 402 disposed at the end of a duct 404 running the length of the chamber 400 below a stretcher 406 that supports the patient 408. Fresh oxygen entering the chamber 400 is directed via a series of nozzles (not pictured) arranged radially around the outlet of the Venturi tube 402 that each point toward a focal point outside of the Venturi tube's outlet. Oxygen forced through the nozzles causes a low pressure area to form within the Venturi tube 402 that pulls air along the duct 404 leading from the opposite end of the chamber 400 and creates a positive pressure and mass gas flow over the patients head. A commercially available example of a Venturi tube 402 suitable for use with some embodiments of the present invention includes the model-120020 "Super Air Amplifier" (12 to 1 ratio) Venturi duct manufactured by the Exair Corporation of Cincinnati, Ohio. In some embodiments, the fresh oxygen discharged through the Venturi tube 402 may be used to cool the chamber via adiabatic gas cooling (by gas expansion). This may be referred to as a Venturi cool tube.

Baffles 410, 412 located at either end of the duct 404 and alongside (not pictured) the stretcher 406 prevent chamber gas flow around the sides and under the stretcher 406 except through the duct 404. The concave ends of the chamber 400 further help redirect the gas flow from the outlet of the duct 404 up towards the patient 408. Thus, cool, dry oxygen, exiting the Venturi tube 402 and re-circulating chamber gas from the duct 404 are directed over the head of the patient 408 and down towards the patient's feet. Water vapor and carbon dioxide exhaled by the patient 408 is mixed with and displaced by the cool, dry oxygen and brought to the exhaust outlet port of the chamber 400.

In steady state operation (i.e. at a constant pressure within the chamber 400), a percentage of the chamber gas (e.g.

~2.5% or 100 liters per minute) is exhausted out the outlet port. The balance of the gas is entrained into the duct 404 and re-circulated back up to the patient head end of the chamber 400. This feature of the present invention permits low (e.g. 100 LPM) volumes of fresh oxygen that have been chilled (e.g., to between 35 and 38 degrees Fahrenheit) to mix with circulating chamber gas to maintain a cool, low humidity and low carbon dioxide environment. A distinct advantage of this system is that there are no moving parts and alternate sources of power (electric/hydraulic), which are contraindicated in an oxygen environment, are not required.

In some embodiments of the present invention, the Venturi induced circulation of oxygen may be enhanced through the use of, for example, one or more explosion-proof electrical, pneumatic, and/or hydraulic driven fans (not pictured) disposed within the duct 404 or elsewhere in the chamber 400. In some embodiments, a Venturi tube may not be used at all and instead one or more fans may be used to circulate the gas.

Figure 5:
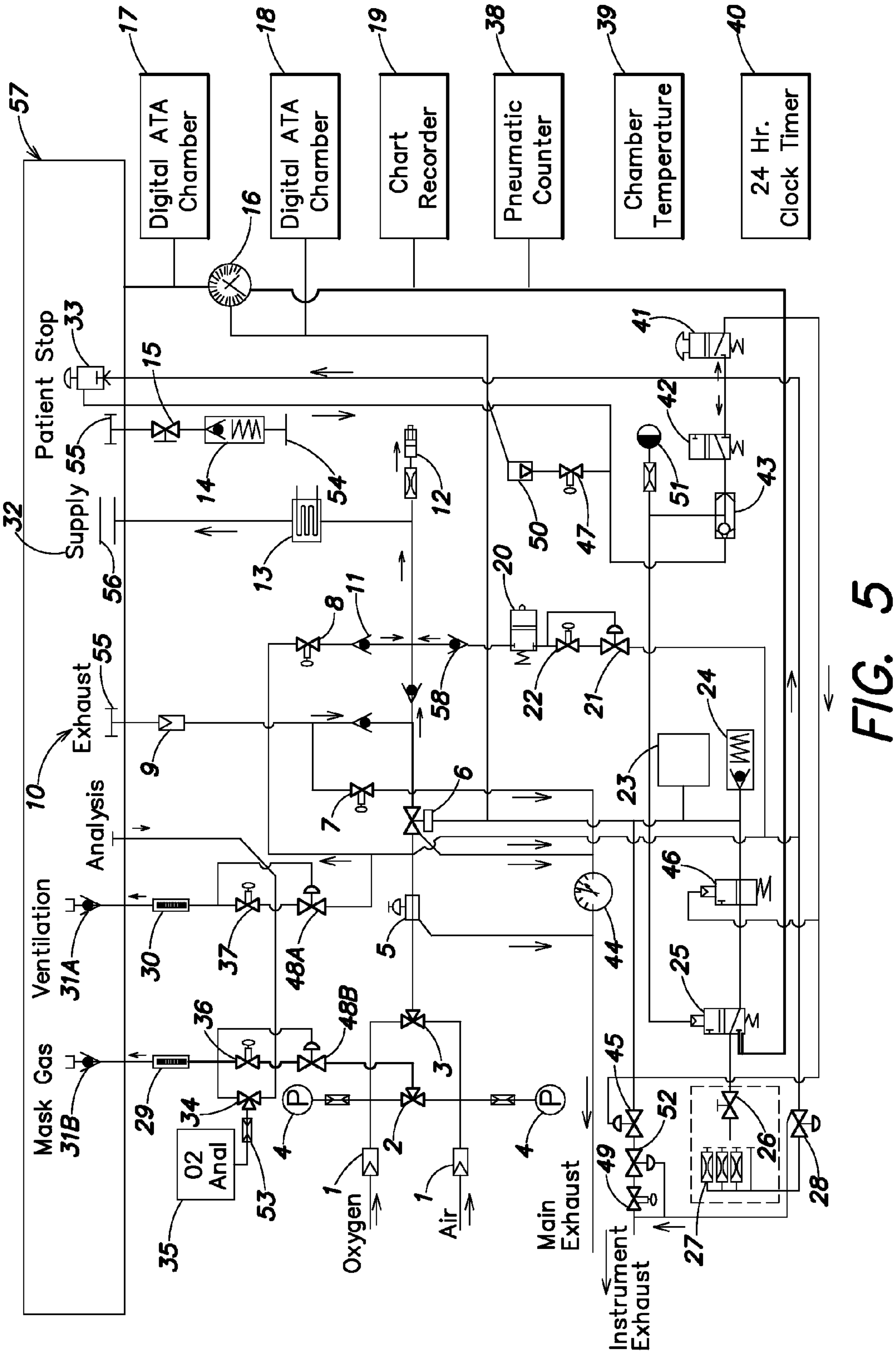
FIG. 5 is a detailed schematic diagram of an example pneumatic control system for a monoplace hyperbaric chamber according to some embodiments of the present invention.

Turning to FIG. 5, a detailed schematic diagram depicting an example hyperbaric chamber control and/or monitoring system is described. This particular example system includes a pressure control subsystem, a primary ventilation circuit, a manual compression valve, a manual decompression valve, an automatic compression/decompression control circuit, an automatic/manual hold function, a patient-activated hold function, an emergency decompression subsystem, an environmental temperature control, a chamber gas mixing feature, a focused ventilation circuit, a mask gas supply subsystem, a gas analysis subsystem, a chamber overpressurization protection subsystem, a suction injury prevention subsystem, a duplex analog pressure gauge, a chamber pressure digital gauge, a pressure/time chart recorder, a pressure cycle counter, temperature monitoring devices, a twenty-four hour clock and timer, and a computer monitoring and control subsystem. As indicated above and as will be explained in more detail below, the active gas cooling systems, temperature monitoring, ventilation subsystems, Venturi gas mixing, and separate ventilation, supply and exhaust circuits described herein result in a lower volume per minute rate of fresh gas ventilation required than prior art monoplace chamber designs.

Note that in any particular embodiment of the present invention not all of these modular subsystems and components of a hyperbaric chamber control and/or monitoring system are required. In fact, many of these subsystems and components may be used individually in combination with, or in sub-combinations with, prior art hyperbaric chambers. Thus, the particular system illustrated in FIG. 5 and described below must be understood to be an example of only some of many possible embodiments of the present invention.

The present invention provides stable gas flow through the use of "referenced flow control." Through out the description of the present invention, it should be noted that many of the subsystems and functions provided in accordance with the present invention may utilize gas flow controllers, for example, upstream and/or downstream gas flow controllers, to ensure stable gas flow. These devices achieve steady, even flow by comparing stable reference pressures (e.g., atmospheric, 35 PSIG regulated, etc.) to variable chamber pressures (e.g., ranging from 1 to 3 ATA). This stable flow allows much safer operation of the hyperbaric chamber in that the operator is not required to continuously monitor and adjust e.g. mask supply gases.

The present invention may use separate supply and exhaust circuits, for example, to improve chamber control and gas circulation and cooling during chamber compression and/or decompression while holding a specific treatment pressure. In some embodiments, the pressure control circuit is a 1:1 forced-balanced volume amplifier that is adapted to supply gas to the chamber or exhaust gas from the chamber through different penetrators, and to utilize a series of flow-control check valves by being supplied with a static reference or set pressure.

The set pressure may be controlled, e.g., by a hand-operated selection valve and orifices of different sizes and/or using a computer control subsystem, to compress or decompress the referenced set pressure at a desired rate (e.g., 1, 3, or 5 PSIG per minute) when set pressure is higher than chamber pressure.

A volume booster may be employed to sense the differential, and to supply gas into the chamber when the set pressure is below chamber pressure. The volume booster may exhaust chamber gas through a separate exhaust system and out through the device to safe atmosphere.

When holding pressure at treatment depth, and referenced set pressure and chamber pressure are the same, the ventilation, which may be activated whenever the chamber door is closed, may be caused to continue to supply gas into the supply circuit and into the chamber. As the chamber pressure increases above reference pressure, for example, by two inches of water in some embodiments (although other pressure changes may be employed), the volume booster may begin to exhaust, so as to compensate for the increase in chamber pressure, and may continue to hold pressure.

Note that throughout this description example values are provided to illustrate operation of the system in some embodiments. It should be understood that these values are not the only possible values or even necessarily average values. Thus, in different embodiments, completely different values, even different relative to each other, may be employed. In other words, even if two example values are in some fixed proportion to each other within a certain range, it is not necessarily true that the proportion will be fixed beyond the range.

Pressure Control Subsystem

Pressurized medical grade oxygen and/or air may be permitted to enter the system through one or more particulate filters 1. A three-way valve 3 with two inlets, each coupled to an outlet of the filters, may be employed to permit selection of either gas to be used to compress and control a patient chamber compartment 57. Coupled to the outlet port of the three-way valve 3, a pressure regulator 5 may be used to reduce a gas input pressure (e.g., 50 to 60 PSIG) to a desired regulated pressure (e.g., approximately 35 PSIG in some embodiments).

The outlet port of the pressure regulator 5 is coupled, among other devices, to a volume booster 6 and ventilation circuits, both of which are described in detail below.

Primary Ventilation Circuit

To provide a stable ventilation flow rate into the patient chamber compartment 57 independent of chamber pressure, an upstream-referenced flow controller 21 may be provided. As indicated above, the inlet port of the flow controller 21 is coupled to the outlet port of the pressure regulator 5. The outlet port of the flow controller 21 may be coupled to a metering valve 22 (e.g., a needle valve) which is coupled to a chamber door activated valve 20. The chamber door activated valve 20 may be biased closed (e.g., so that flow of ventilation gas is prevented), for example, using a spring bias. Coupled to the outlet of the chamber door activated valve 20 is a check valve 58 that permits only one-way flow of the ventilation gas toward the chamber 57. The outlet of the check valve 58 may be coupled to a door safety lock 12 and a heat exchanger 13 that leads to the chamber 57.

The chamber door may be configured so that upon closure, a valve plunger of the chamber door activated valve 20 is activated and thereby allows ventilation gas to pass through the chamber door activated valve 20 from the flow controller 21, pass through the check valve 58, slide a bolt (e.g., ram) of the door safety lock 12, and/or pass through the heat exchanger 13 to the inlet port of the chamber 57.

The actual rate at which the ventilation gas flows may be adjustable. As indicated above, the control port of the flow controller 21 is coupled to the outlet of the upstream metering valve 22 to provide a feedback reference pressure level (e.g., 35 PSIG). An example of a flow controller 21 that may be suitable for use with some embodiments of the present invention includes the Model 63D Constant Differential Flow Controller manufactured by Siemens Energy & Automation, Inc. of Alpharetta, Ga.

The heat exchanger 13 may operate in the same manner and serve the same functions as described above with reference to FIG. 3. More details regarding the heat exchanger 13 are provided below in the discussion regarding environmental temperature control.

Manual Compression Valve

The outlet port of the pressure regulator 5 may also be coupled to a manual compression valve 8. Regulated gas (e.g., 35 PSIG gas in some embodiments, although other pressures may be employed) may be caused to flow from the pressure regulator 5 directly to a manual compression or similar control valve 8, from which the gas may be caused to flow through a check valve 11 and into the patient chamber compartment 57.

Manual Decompression Valve

Decompression of the patient chamber compartment 57 may be provided via an exhaust subsystem 10. For example, in some embodiments, the exhaust subsystem 10 may include a safety suction "T" 55, an exhaust port, a lint/particulate filter 9 coupled to the exhaust port downstream of the suction "T" 55, a manual decompression valve 7 coupled to the outlet of the filter 9, and a chamber exhaust flow meter 44 downstream of the decompression valve 7 in the line leading to safe atmosphere.

A significant cause of malfunctions in prior art chamber pressure and/or ventilation control systems is due to the accumulation of foreign matter in the system's valves and other devices. This problem has resulted in significant repair costs associated with prior art chambers. The present invention solves this problem through the use of a particulate filter 9 (e.g., a 5 micron filter) designed to trap linen lint and other debris that may otherwise accumulate in the system.

Automatic Compression/Decompression Control Circuit

In the example depicted in FIG. 5, the inlet port of a volume booster relay 6 is coupled to the outlet port of the pressure regulator 5 so that the volume booster relay 6 may be employed to add regulated (e.g., 35 PSIG) gas to the patient chamber compartment 57 and/or to exhaust gas from the patient chamber compartment 57 based on the pressure within the compartment as compared to the desired chamber pressure indicated on a set point controller 28. The signal port of the volume booster relay 6 is coupled to the outlet port of, for example, a multi-way selection valve 26 (e.g., a four-way valve is pictured) whose inlet ports are coupled to the outlet port of the set point controller via differently sized sonic orifice restrictors and trimmer metering valves 27.

The set point controller 28, which may be manually adjustable or computer controlled, may be employed along with the multi-way selecting valve 26 to set a rate of pressure change in the patient chamber compartment 57. For example, the set point controller 28 may be used in conjunction with the multi-way selecting valve 26 to permit selection from among a choice of various rates (e.g., 0.25 PSIG/min., 1 PSIG/min., 3 PSIG/min., and/or 5 PSIG/min.) by routing set point pressure gas through, for example, different sonic orifice restrictors and trimmer metering valves 27, an infinitely variable regulator, or a set of pre-set regulator valves. In some embodiments, instead of (or in addition to) the multi-way valve and different sonic orifices, the set point controller 28 may simply be coupled to a computer controlled regulator that allows infinite selection of gas flow rates from zero to the maximum system rate.

A safety relief valve 24 (e.g., a 32 PSIG or other set point relief valve) may be coupled to the volume booster relay signal line to prevent unacceptably high set point pressures from reaching the volume booster relay 6 and/or to prevent over-pressurization of the patient chamber compartment 57.

In some embodiments that use a multi-way selection valve 26, the set point pressure control signals that are sent to the volume booster relay 6, may be buffered to minimize transitory pressure spikes that result from switching between different sonic orifices. A rate volume tank 23 may be coupled to the volume booster relay signal line for such a purpose. As depicted in FIG. 5, a one liter sized rate volume tank 23 is an example of a size that may be suitable with a system operating with the example pressures and flow rates provided in the discussion of this illustrative embodiment of the present invention.

Automatic/Manual Hold Function

In some embodiments, a three-way valve 25 may be disposed within the volume booster relay signal line between the multi-way rate selection valve 26 and the volume booster relay 6 to enable and/or isolate set point pressure gas through the multi-way rate selection valve 26. The three-way valve 25 may be biased open (e.g., via a spring or other bias) to allow passage of set point pressure gas through the multi-way rate selection valve 26. An operator may be permitted to manually activate (e.g., close) the three-way valve 25. For example, the three-way valve 25 may be adapted to be activated via a control signal, and a toggle (or similar) valve 42, coupled to the regulated gas supply and adapted to provide such a signal, may also be provided. The toggle valve 42 may be biased (e.g., via a spring or other bias) closed (e.g., preventing downstream pressurization), and may be further adapted to be manually activated (e.g., opened) by the operator.

Patient-Activated Hold Function

In some embodiments, a patient within the patient chamber compartment 57 may be permitted to independently interrupt or temporarily pause compression of the chamber, for example, in the event he/she is unable to equalize. A patient hold valve 33 may be provided within the chamber 57 for this purpose. For example, a patient hold valve 33 may be embodied as a push-button (or similar) valve coupled to the regulated gas supply and thereby adapted to provide a control signal.

In some embodiments, the patient hold valve 33 may be biased (e.g. via a spring or other bias) closed (e.g., preventing downstream pressurization) and may be further adapted to be manually activated (e.g., opened) by the patient, permitting a control signal to be delivered via a valve 43 (e.g., a shuttle valve coupled to the push-button valve) to the control port of the three-way valve 25 thereby activating the three-way valve 25. In the example embodiment depicted in FIG. 5, a patient activating the patient hold valve 33 will thus, block transmission of a compression/decompression change signal to the volume booster relay 6 by isolating the rate control selection valve 26 and the sonic orifices 27, and finally venting the volume booster relay signal via the exhaust port of the manual set point controller 28.

The signal line from the patient hold valve 33 may be decompressed by venting this static line to the atmosphere when the patient hold valve 33 is not being activated by the patient. For example, a metering vent valve 47 (e.g., a needle valve) may be provided, and may be tuned to a value of less capacity than the patient stop valve 33 so that the patient stop circuit remains activated as long as the patient hold valve 33 is being depressed by the patient. As soon as the patient releases the patient hold valve 33, compression/decompression may be allowed to resume.

The operator may be provided with respective audio and/or visual alerts or alarms, for example, via a pneumatic sonic alarm 50 in conjunction with a pneumatic visual (e.g., red/green) indicator 51 that indicates that the patient has activated the patient stop circuit. The visual indicator 51 may serve as a hold/run condition indicator to indicate that the three-way valve 25 is pressurized (e.g., activated and closed), meaning that either the patient hold button 33 has been activated, or the operator-controlled manual toggle valve 42 has been activated, to stop chamber pressurization or depressurization. Other alarms may be employed.

Thus, the patient hold valve 33 permits a patient inside the chamber undergoing treatment to stop chamber compression or decompression for a patient determined duration (e.g., via depression of a push button valve for the duration of the button depression). In some embodiments, simply activating a push button may suspend compression/decompression until the operator or computer control subsystem resets the patient hold valve 33 to resume the compression/decompression. A patient thereby may interrupt pressure change, for example, if he or she is unable to equalize sinus and/or ear pressure. The inclusion of a patient hold valve 33 may significantly improve patient compliance and willingness to continue a course of therapy. In some embodiments, an operator outside of the chamber may override this function.

Emergency Decompression Subsystem

The system may further provide for emergency decompression of the patient chamber compartment 57. For example, emergency decompression may be accomplished via an appropriate valve such as, for example, a spring-biased three-way momentary push-button valve 41, which may be supplied by regulated (e.g., 35 PSIG) oxygen (i.e., coupled to the outlet port of the pressure regulator 5). The outlet of the momentary push-button valve 41 is coupled to the control port of a three-way valve 46. Manual activation of the momentary push-button valve 41 may produce a control signal so as to activate the three-way valve 46. While the three-way valve 46 may be biased open, e.g., via a spring bias, enabling passage of set point pressure gas through the multi-way rate selection valve 26, activation of the three-way valve 46 may isolate set pressure from the rate-control selection valves 26, 27.

The same control signal that may activate the three-way valve 46 may be further employed to activate a pneumatic on/off valve 45, which may allow set pressure to vent to atmosphere at a controlled rate through an adjustable needle valve 49. In some embodiments, a downstream atmospheric-referenced flow controller 52 may be included to provide a fixed supply pressure to the metering valve 49 so as to ensure a linear ascent rate (i.e., linear depressurization).

Environmental Temperature Control

Environmental temperature control within the patient chamber compartment 57 may be achieved by utilizing a heat exchanger 13 (e.g., a flat-plate heat exchanger or similar heat exchanger) to cool ventilation supply oxygen and/or compression supply oxygen. As indicated above, a heat exchanger 13 may be disposed in the line leading from the outlet port of the volume booster relay 6 and the ventilation circuit 20, 21, 22. The gas flowing through the heat exchanger 13 may be cooled via a number of different methods. For example, these methods may include any combination of a combined chiller/heater closed-circuit pump system with a reservoir; an open- or closed-circuit chill water; and/or an open circuit bleed of carbon dioxide from a high-pressure cylinder wherein as the carbon dioxide expands it adiabatically cools the oxygen in the exchanger without mixing with it (e.g., via conduction) and then vents to safe atmosphere without entering the patient chamber compartment 57. The inventor has observed that, by the use of methods and apparatus in accordance with the present invention, patient chamber compartment temperatures between 50 to 80 degrees Fahrenheit may be achieved.

Chamber Gas Mixing Feature

As described above with reference to FIG. 4, a gas-mixing Venturi 56 may be employed to entrain chamber gas through a duct 404 (FIG. 4) within the chamber 57. For example, in some embodiments, approximately forty volumes (or other suitable volume) of chamber gas may be entrained for each volume of fresh gas supplied through the flat-plate heat exchanger 13. Gas discharged from the Venturi 56 may be directed to flow around a shell of the Venturi 56, e.g., in a counter-clockwise direction, to maximize gas distribution and mixing through a combination of the Venturi 56, the shape of the patient chamber compartment 57, and the Coriolis effect. Maximizing gas distribution and mixing in this manner keeps the chamber temperature at a desired set point and carbon dioxide and humidity produced by the patient at a minimum. This permits the chamber control and/or monitoring system to utilize a minimum of fresh gas per minute while still maintaining total environmental control within the patient chamber compartment 57.

As indicated above, Venturi induced circulation of oxygen along the long axis of the chamber is accomplished by the Venturi and a ducting/baffle system that creates a positive pressure and mass gas flow over the patients head and down towards the feet. The inlet of the Venturi duct is located at the patients feet where gas is exhausted out of the chamber (e.g. at 100 liters per minute) and the balance of gas is entrained into the Venturi duct and re-circulated back up to the patient head end of the chamber. This feature permits low (e.g. 100 LPM) volumes of fresh oxygen that have been chilled (e.g. to 35 to 38 degrees Fahrenheit) to mix with circulating chamber gas to maintain a cool, low humidity and low carbon dioxide environment. An advantage of this system is that there are no moving parts that require alternate sources of power which are potentially dangerous in an oxygen-rich environment.

Focused Ventilation Circuit

When a patient experiences cool air blowing on his/her face, a normal physiological response, called "diver's reflex," results that typically causes the body to cool the trunk by sending blood to the extremities. The present invention takes advantage of this reflex by providing the patient with a focused ventilation circuit.

A flexible adjustment hose (not shown) inside the chamber 57 may be adjusted by the patient to direct oxygen to the face or other area of the patient's body. For example, oxygen at thirty-five PSIG may be delivered through a filter 1 to an upstream-referenced flow controller 48A. The flow rate control may be adjusted by a metering valve 37. The actual flow may be visualized through a flow meter 30 coupled to the outlet of the metering valve 37. A check valve 31A disposed in the flexible adjustment hose may be employed to prevent reverse flow. In some embodiments, the flexible adjustment hose may be supported by an articulating support arm that holds the opening of the hose in position.

Mask Gas Supply Subsystem

A mask gas selection valve 2 may be employed to select either oxygen or air. The air and oxygen may be passed through filters 1 and the pressure may be monitored through gauges 4. The outlets of the filters 1 are coupled to the inlet of an upstream-referenced flow controller 48B. The flow rate to the mask may be adjusted using a metering valve 36 coupled to the outlet of the flow controller 48B. The actual flow may be visualized through a flow meter 29 disposed within the line leading to the chamber 57. A check valve 31B in a flexible adjustment hose coupled to the mask may be employed to prevent reverse flow.

Gas Analysis

In some embodiments, a fuel cell analyzer 35 (e.g., battery or otherwise powered) may be employed to receive gas from a selector valve 34. The gas received may be, e.g., either air or oxygen flowing through the mask gas supply circuit, or gas drawn for analysis from within the patient chamber compartment 57. As pictured in FIG. 5, one of the inlet ports of the selector valve 34 may tap into the mask gas supply circuit, for example, between the metering valve 36 and flow meter 29. The second inlet port of the selector valve 34 may tap directly into the chamber 57. The analyzer 35 may be employed to monitor the oxygen content of the mask gas and/or the chamber.

In some embodiments, a sonic orifice 53 may be located downstream of the selection valve 34 to ensure a desired flow rate (e.g., 100 cc/min or some other desired rate) into the analyzer 35. In addition, an oxygen cell (e.g., a Clarke cell) may be provided that is referenced to atmosphere to reduce and/or prevent miscalibration and/or false readings.

In some embodiments, information output by the analyzer 35 may be fed to a computer control system which may respond to any readings that are outside an acceptable range. For example, if the analyzer 35 detects that the oxygen level is too low, the rate of oxygen being added to the chamber 57 may be increased. In some embodiments, the analyzer may be used to ensure that the proper gas is being supplied via the mask. A computer monitoring and control subsystem may verify the operation of a selection valve 2 by using the output of the analyzer 35 to confirm the gas being supplied.

Chamber Over-Pressurization Protection

In some embodiments, a relief valve 14 may be connected to the patient chamber compartment 57 via a suction prevention safety device 55. For example, in some embodiments, an American Society of Mechanical Engineers (ASME) certified, thirty five PSIG pre-set pressure relief valve 14 may be used. A shut-off valve 15, such as for example, a hit-to-close or ball shut-off valve, may be installed between the relief valve 14 and the patient chamber compartment 57. Such a shut-off valve 15 meets the ASME's pressure vessels for human occupancy (PVHO) standard requirement to protect against a failure of the relief valve 14 to close after relieving excess pressure. In some embodiments, a reaction nozzle 54, such as for example a T-shaped reaction nozzle, may be coupled to the relief valve 14 to prevent thrusting by a unidirectional gas flow.

Suction Injury Prevention

In some embodiments, a suction-prevention safety device fitting 55 (e.g., a cross-shaped or otherwise shaped fitting) may be placed on both the chamber exhaust circuit 10 and the chamber over-pressurization circuit to minimize the risk of patient suction injury or entrainment of linen or other material which might restrict or otherwise cut-off gas flow.

Duplex Analog Pressure Gauge

Prior art pneumatic chamber systems typically utilize separate chamber pressure and reference “set” pressure gauges, a practice which may induce operator error. To minimize operator error, a duplex analog pressure gauge 16 may be employed to simultaneously show chamber and set pressure on the same dial. A duplex analog pressure gauge 16 includes a single gauge face (e.g., showing a range of 1 to 3 ATA) and two independent needles operating within concentric shafts connected to two independent Bourden tube drive mechanisms. As shown in FIG. 5, one needle circuit may be coupled to display the chamber pressure while the other needle circuit may be coupled to display the reference “set” pressure.

The use of a duplex analog pressure gauge 16 permits the operator to more easily and intuitively compare pressure and rate of change information as between the patient chamber compartment pressure and the reference “set” pressure. This helps the operator to avoid “over shooting” the set pressure as well as other potential mistakes that are commonly made in the manual operation of prior art systems. Thus, when used in conjunction with the numerical readouts from a digital gauge, the combined pressure monitoring and management benefits of the duplex analog pressure gauge 16 improve operator productivity and minimize operator error as compared to other presently commercially available systems.

Chamber Pressure Digital Gauge

In some embodiments, a digital gauge 17 may be employed to provide a very accurate digital chamber pressure read-out (e.g. in the range of 1 to 3 ATA) for visualization from a large distance (e.g., up to 30 feet away). To minimize operator error, the present invention may be embodied using a single gauge face with two independent digital readouts. As with the analog gauge, one digital output pressure measurement circuit may be coupled to display the chamber pressure while the other digital output pressure measurement circuit may be coupled to display the reference “set” pressure. This use of a digital gauge 17 permits the operator to more easily compare pressure and rate of change information as between the patient chamber compartment pressure and the reference “set” pressure. This helps the operator to avoid “over shooting” the set pressure as well as other potential mistakes that are commonly made in the manual operation of prior art systems.

Pressure/Time Chart Recorder

A pressure/time chart recorder 19 may be employed to produce a paper strip or other method of recording the period of time the chamber is under pressure during a treatment (e.g., door open-door closed). The pressure/time chart recorder 19 may be coupled to a port leading directly into the chamber 57. Use of such a recorder 19 meets the Centers for Medicare/Medicaid Services (CMS) standard for independent documentation of time under pressure (e.g., which is measured in units of 30 minute duration, plus any partial units), which in turn determines CMS payment.

Pressure Cycle Counter

A pressure cycle counter 38, e.g., a digital odometer-type mechanical device, may be employed to count the number of times the chamber makes excursions from atmospheric pressure to higher gauge pressure, e.g., irrespective of that final gauge pressure. The pressure cycle counter 38 may be coupled to a port leading directly into the chamber 57. This feature facilitates the scheduling of preventive maintenance dictated by the number of times the system is pressurized. Information output by the pressure cycle counter 38 may be used by a computer control subsystem to automatically perform machine diagnostic testing of the chamber 57 and/or to perform automated preventive and/or required maintenance.

Temperature Monitoring Devices

One or more temperature monitoring devices 39 may be employed to monitor the temperature of the gas of the patient chamber compartment 57 and/or the patient's body temperature. For example, two thermocouple devices may be mounted on a exterior of the supply pipe between the heat exchanger 13 and the Venturi 56. These thermocouples may be in contact with the pipe and fully insulated from atmospheric air temperature. One or more duplicative devices may be attached on a chamber exhaust (e.g., between the suction safety device 55 and the external lint filter 9) and mounted and/or insulated in a similar fashion to those of the supply pipe. Both supply and exhaust thermocouples may provide digital readouts in Fahrenheit and/or Centigrade and the information output may be utilized by an operator and/or computer control to provide chamber monitoring and control of chamber gas temperature. Likewise, a thermal probe attached to the patient may provide information used to determined, for example, that the temperature in the chamber should be lowered.

24 Hour Clock and Timer

A clock and/or timer 40 may be employed to time the treatment under pressure as well as air breaks, and/or to provide for other timing requirements. The clock and/or timer 40 may be, for example, a battery operated or other 24 hour clock with count up and/or count down features. The clock and/or timer 40 may be coupled to other measurement devices, as well as the chamber door, to receive information indicating the occurrence of various events. The clock and/or timer 40 may also be coupled to a computer controller to output information useful in the operation of the various subsystems and functions described herein. Thus, the clock and/or timer may be used to help automatically perform treatments using the hyperbaric chamber 57 of the present invention.

Computer Monitoring and Control Subsystem

As indicated above, in some embodiments, pneumatic control signals may be generated via electric-to-pneumatic transducers that are driven by a computer-based process controller. A commercially available example of an electric-to-pneumatic transducer suitable for use in some embodiments (particularly computer controlled embodiments) of the present invention includes the explosion-proof Model 6000 Electro-Pneumatic Transducers manufactured by the Fairchild Industrial Products Company of Winston-Salem, N.C. Throughout the pneumatic circuits of the present invention described herein, the manual controls for valves and other devices may be replaced with electric-to-pneumatic transducers driven by a computer-based process controller. In some embodiments, pneumatic control signal lines may run from the valves and other devices to a centralized compartment that is isolated from explosive/flammable gases.

A computer-based process controller may produce an infinite number of combinations of rates of compression/decompression, durations of treatment, and treatment pressures, and/or may provide a series of alarms to notify the operator of important events during the sequence of treatment, such as air mask breaks, etc.

The different combinations and sequences of applying the possible treatment parameters for a given treatment are referred to herein as a treatment profile. FIG. 6 illustrates an example of a representation of a treatment profile display output by an embodiment of a computer control and monitoring subsystem of the present invention. The solid graph line represents the treatment profile that a physician approved for a patient based upon a computer selected recommendation, i.e., the prescribed treatment profile. In the depicted example, the prescribed treatment profile is 3.0 ATA for 90 minutes. The dotted graph line represents a plot of the real time measurements of the chamber pressure during treatment, i.e., the actual treatment profile.

In addition to the electric-to-pneumatic transducers discussed above, the computer monitoring and control subsystem may be embodied using a personal computer (PC) (e.g., an Intel Pentium processor based system) running a program specific to the present invention on a standard operating system such as Microsoft® Windows XP®. In some embodiments, a computer and operating system capable of real time processing may be used to execute very precise treatment profiles. In some embodiments, the PC or computer may include hardware interfaces that may facilitate connection to the electric-to-pneumatic transducers and various feedback sensors, detectors, input devices, and/or measurement devices.

Figure 7:
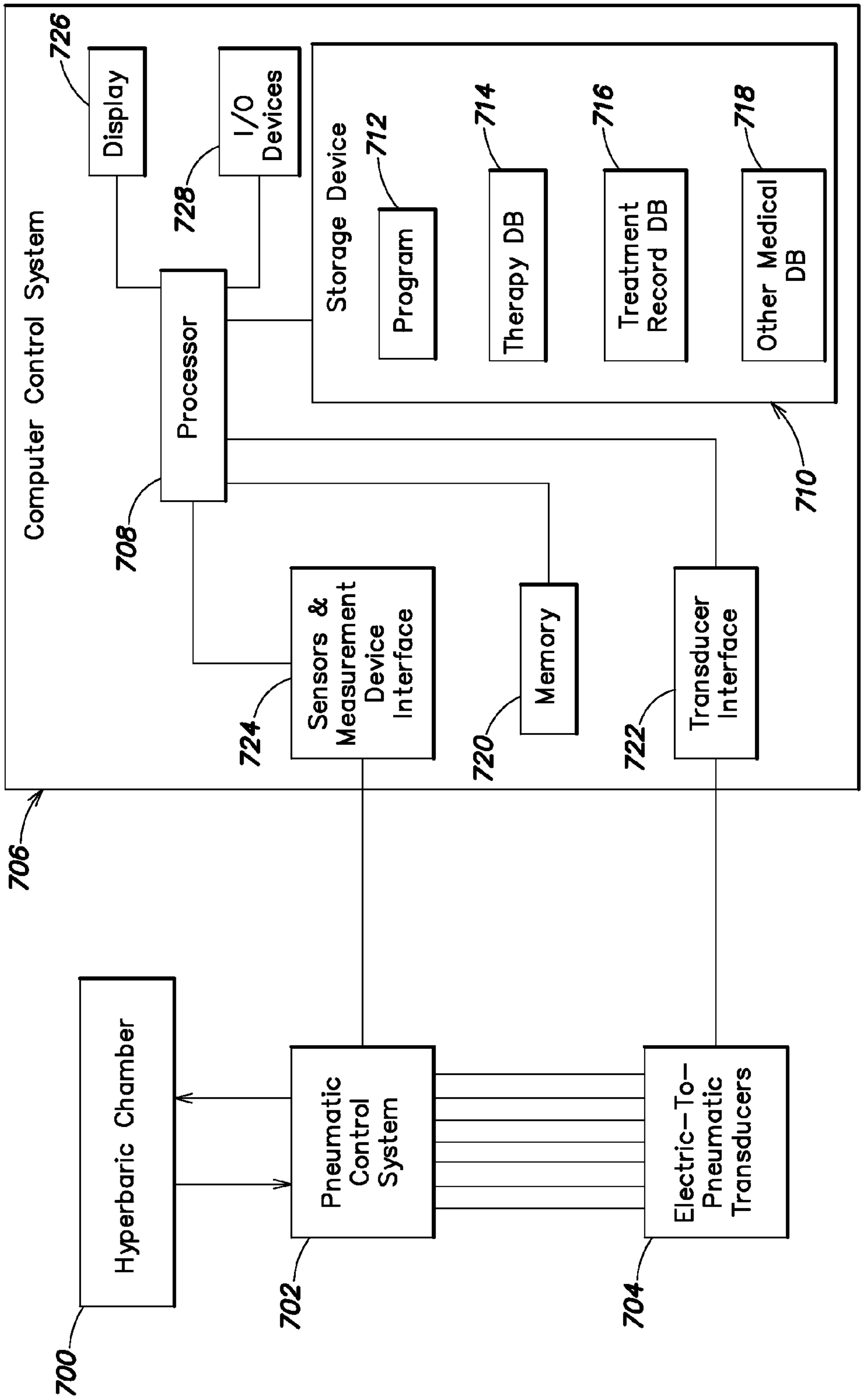
FIG. 7 is a block diagram illustrating an example of a computer controlled hyperbaric chamber monitoring and control system according to some embodiments of the present invention.

Referring to FIG. 7, a computer controlled hyperbaric chamber monitoring and control system includes a hyperbaric chamber 700 coupled to a pneumatic control (and monitoring) system 702 as described in detail above. In some embodiments, the various control valves and devices of the pneumatic control system 702 are each coupled to electric-to-pneumatic transducers 704. In some embodiments of the pneumatic control (and monitoring) system 702, particularly those including measurement instruments, digital gauges, and other information generating devices, the computer control system 706 may be directly coupled to portions of the pneumatic control (and monitoring) system 702 via a sensors and measurement device interface 724. The electric-to-pneumatic transducers 704 are coupled to the computer control system 706 via a transducer interface 722.

The computer control system 706 includes a processor 708 coupled to a storage device 710. The storage device 710 which may be embodied as a hard disk drive or any suitable information storage and retrieval system (including local and/or remote systems), includes a program 712 that will be described in more detail below. In addition to the program 712, several databases 714, 716, 718 may be stored on the storage device 710. The databases 714, 716, 718 are described below. The computer control system 706 further includes memory 720, display devices 726 such as a monitor, and input/output (I/O) devices 728 such as a keyboard, mouse, network cards, modems, serial ports, and the like. The display devices 726 are operable to display the program's interface, an example portion of which is depicted in FIG. 6.

The program 712 may include (or may access) a therapy database 714 of hyperbaric therapy policies and procedures used in treating patients, including associated treatment profiles. A search engine included as part of the program 712 permits the operator to easily find all the information within the databases 714, 716, 718 on a given subject. In addition to the therapy database 714, the program 712 includes (or may access) a treatment record database 716 wherein information regarding the medical history and prior treatments of each patient is documented. This data may be retrieved and displayed when the patient is treated by merely entering the patient name or other identification information. The program 712 may include (or may access) other medical databases 714 stored locally or available online via, for example, the Internet or other network.

Figure 8:
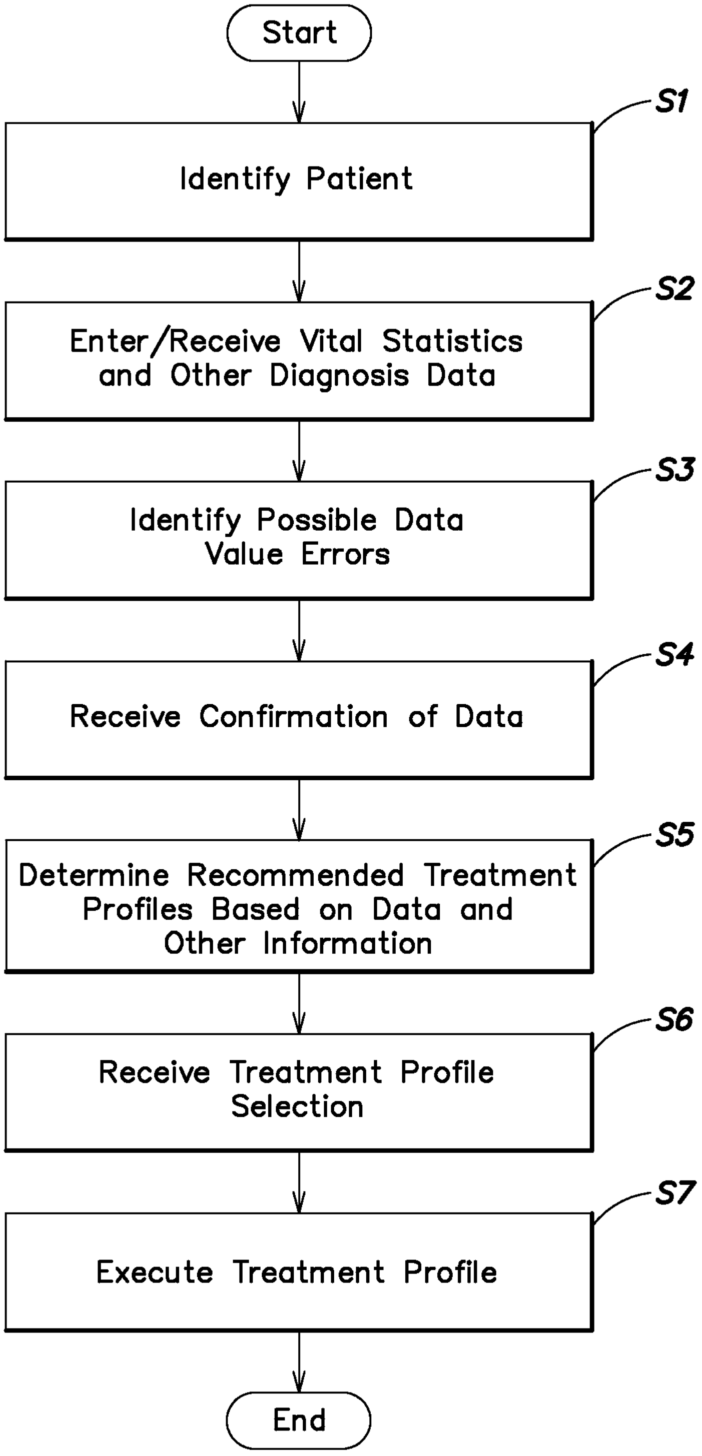
FIG. 8 is a flowchart illustrating an example program control method according to some embodiments of the present invention.

Referring now to FIG. 8, operation of the program 712 is now described. At the start of a treatment session, the program 712 may prompt the operator for patient identifying information. This corresponds to Step S1 in the flowchart of FIG. 8. The program 712 may display any prior treatment data and then prompt the operator to enter specific vital sign information of the patient. In some embodiments, the data may be entered manually. In some embodiments, measurement devices coupled to the computer 706 via the hardware interfaces 722, 724, automatically supply the data requested by the program 712. The system receives the data in Step S2.

If any value provided is outside an acceptable range of preset parameters, the program 712 will notify the operator to check for an error condition in Step S3. For example, an automated blood pressure measurement cuff may be out of place or the operator may have made a data entry typographical error. If the operator confirms the questioned values in Step S4, the program 712 identifies the questioned values as being outside normal physiological parameters. Based on the entered data, stored patient records from the treatment record database 716, any manually adjusted parameters altered by the operator/doctor, and stored data from the therapy database 714, the program 712 recommends a treatment profile specifically tailored for the patient and/or best suited for the particular diagnosis in Step S5.

The program 712 may be configured to recommend a range of treatments including conservative through aggressive approaches. A doctor reviews the program recommended treatment profile or profiles and selects the most appropriate treatment in Step S6. The patient enters the hyperbaric chamber 700 of the present invention. The chamber 700 is sealed. The identity of the patient and the prescribed treatment profile are confirmed and the program 712 initiates treatment in Step S7.

Referring back to FIG. 6, the following specific hypothetical example is provided merely for illustrative purposes. In this example, the patient, Jane Doe, has been diagnosed as having Gas Gangrene (ICD-9 40.0) which should be treated at 3.0 ATA for 100 minutes under ideal conditions. However, the patient has a high fever (e.g., 103 degrees Fahrenheit) that increases risk for grand mal seizure and is also unable to wear air mask for air breaks to reduce seizure risk.

Based upon this data and other stored information, the program recommends two possible treatment profiles: (A) 2.5 ATA for 100 minutes; and (B) 3.0 ATA for 70 minutes maximum. If the patient has other physiological parameters out of specification, the program will alert operator and make further recommendations.

Upon receiving the operator's/doctor's selection of treatment profile (B), the system of the present invention executes the treatment profile and monitors its progress. FIG. 6 displays the prescribed treatment profile (solid plot) and the actual treatment profile (dotted plot) for Jane Doe. The difference between the prescribed and actual treatment profiles is due to an eight minute hold that occurred at approximately fifteen minutes into the treatment. In this hypothetical example, the patient, Jane Doe, experienced difficulty equalizing her left ear at approximately two atmospheres of pressure. Ms. Doe immediately activated the patient hold valve 33 which automatically suspended further compression of the chamber 57. After approximately eight minutes, the patient was able to equalize and indicated such to the operator who reset the patient hold valve 33 and allowed the system to resume pressurization according to the prescribed treatment profile.

In an effort to minimize any impact on the total length of the treatment, the computer control subsystem of the present invention automatically increased the rate of pressurization very slightly so that the set point pressure (i.e., 3.0 ATA) was reached four minutes sooner than if the original rate of pressurization had been followed after the eight minute hold.

As indicated above, the system may dynamically adapt the actual treatment profile to any events that prevent following the prescribed treatment profile. The adaptation may be designed to cause the actual treatment profile to match the prescribed profile as much as possible or it may be designed to follow the most conservative adaptation possible. For example, the program may terminate the treatment early if a patient repeatedly activates the patient hold valve or shows a significant body temperature increase.

In some embodiments, other therapies including LASER and near infrared light therapies, that may be conducted in a hyperbaric chamber, may also be profiled and automated or semi-automated using the systems and/or in conjunction with the systems of the present invention. Therapies using LASER and near infrared light suitable for being adapted to be conducted in a hyperbaric chamber according to the present invention are described in U.S. patent application Ser. No. 10/726,040, filed Dec. 2, 2003 and titled "Methods and Apparatus for Light Therapy", which is hereby incorporated herein by reference in it entirety for all purposes. The use of a computer controlled light emitting diode (LED) near infrared light source that may operate inside or outside the hyperbaric chamber pressure barrier is disclosed in the above referenced patent application. The combined computer control system of the present invention and the LED near infrared therapy control system permits an operator to select a combined therapy profile that both controls the hyperbaric chamber pressure parameters and the light frequency, duration and intensity of the light exposure, to create a combined treatment profile.

Conclusion

It will be understood that other ventilation circuits, flow controllers, valve types/sizes, volumes, gas compositions, and pressures than those disclosed herein may be employed, and that the unique features provided by the methods and apparatus of the present invention are not limited in their expression to the embodiments described herein. For example, where spring-loaded valves are disclosed, other biasing means may be substituted. As well, where a flat plate heat exchanger is disclosed, any number of other types of heat exchangers may be utilized. Further, where coaxially-rotated indicator needles are disclosed, side-by-side indicators may be substituted.

Accordingly, while the present invention has been disclosed in connection with the preferred embodiments thereof, it should be understood that other embodiments may fall within the spirit and scope of the invention, as defined by the following claims.

What is claimed is:

1. An apparatus comprising:

a hyperbaric chamber;

a set pressure selection valve having an inlet operable to be coupled to a gas supply;

a control system including a volume booster adapted to provide both oxygen to pressurize the hyperbaric chamber and controlled exhaust of the hyperbaric chamber, the volume booster having an inlet port operable to be coupled to a pressurized gas supply, an outlet port coupled to the hyperbaric chamber, and a reference port coupled to an outlet port of a set pressure selection valve; and a duplex analog pressure gauge having a first needle circuit coupled to the hyperbaric chamber and a second needle circuit coupled to the outlet port of the set pressure selection valve, wherein the control system is adapted to provide the controlled exhaust of the hyperbaric chamber concurrently with the set pressure selection valve maintaining a pressure of the hyperbaric chamber.

2. The apparatus of claim 1 wherein the set pressure selection valve includes a computer controlled regulator valve.

3. An apparatus comprising:

a monoplace hyperbaric chamber;

a control system including a volume booster adapted to provide both oxygen to pressurize the monoplace hyperbaric chamber and controlled exhaust of the monoplace hyperbaric chamber, the volume booster including:

an inlet port operable to be coupled to a pressurized gas supply, an outlet port coupled to the hyperbaric chamber, and a reference port; and a set pressure selection valve having an outlet port coupled to the reference port of the flow controller, wherein the control system is adapted to provide the controlled exhaust of the hyperbaric chamber concurrently with the set pressure selection valve maintaining a pressure of the hyperbaric chamber.

4. The apparatus of claim 3 wherein the set pressure selection valve includes an inlet operable to be coupled to a gas supply and includes a computer controlled regulator valve.

5. The apparatus of claim 3 further comprising a pressure gauge coupled to the hyperbaric chamber and to the outlet port of the set pressure selection valve.

6. The apparatus of claim 5 wherein the pressure gauge includes a duplex analog pressure gauge having a first needle circuit coupled to the hyperbaric chamber and a second needle circuit coupled to the outlet port of the set pressure selection valve.

7. A method of regulating pressure in a monoplace hyperbaric chamber comprising:

providing a monoplace hyperbaric chamber;

controlling flow of a pressurized gas using a control system including a volume booster adapted to provide both oxygen to pressurize the monoplace hyperbaric chamber and controlled exhaust of the monoplace hyperbaric chamber, the volume booster including an inlet port coupled to a pressurized gas supply, an outlet port coupled to the monoplace hyperbaric chamber, and a reference port;

selecting a set pressure using a set pressure selection valve having an outlet port coupled to the reference port of the flow controller; and monitoring pressure in the monoplace hyperbaric chamber using a pressure gauge coupled to the hyperbaric chamber and to the outlet port of the set pressure selection valve wherein the pressure gauge includes a duplex analog pressure gauge having a first needle circuit coupled to the monoplace hyperbaric chamber and a second needle circuit coupled to the outlet port of the set pressure selection valve, wherein the control system is adapted to provide the controlled exhaust of the hyperbaric chamber concurrently with the set pressure selection valve maintaining a pressure of the hyperbaric chamber.

* * * * *